(12) United States Patent
Brannan et al.

(10) Patent No.: US 9,526,569 B2
(45) Date of Patent: *Dec. 27, 2016

(54) ELECTROSURGICAL INSTRUMENT

(71) Applicant: COVIDIEN LP, Mansfield, MA (US)

(72) Inventors: Joseph D. Brannan, Lyons, CO (US); Casey M. Ladtkow, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/954,996

(22) Filed: Nov. 30, 2015

(65) Prior Publication Data

US 2016/0081743 A1 Mar. 24, 2016

Related U.S. Application Data

(63) Continuation of application No. 14/564,896, filed on Dec. 9, 2014, now Pat. No. 9,198,721, which is a
(Continued)

(51) Int. Cl.
*A61B 18/04* (2006.01)
*A61B 18/14* (2006.01)
(Continued)

(52) U.S. Cl.
CPC ....... *A61B 18/1477* (2013.01); *A61B 18/1815* (2013.01); *A61B 2018/00601* (2013.01);
(Continued)

(58) Field of Classification Search
CPC ......... A61B 18/00; A61B 18/12; A61B 18/18; A61B 18/1815; A61B 2018/18; A61B 2018/1815; A61N 5/00; A61N 5/02; A61N 5/022; A61N 2005/0643
See application file for complete search history.

(56) References Cited

U.S. PATENT DOCUMENTS

D223,367 S 4/1972 Kountz
D263,020 S 2/1982 Rau, III
(Continued)

FOREIGN PATENT DOCUMENTS

CN 1103807 A 6/1995
CN 1283087 A 2/2001
(Continued)

OTHER PUBLICATIONS

European Search Report EP 04752343.6 dated Jul. 31, 2007.
(Continued)

*Primary Examiner* — Robert N Wieland

(57) ABSTRACT

An electrosurgical instrument includes an elongated housing having proximal and distal ends. The proximal end is configured to couple to a source of electrosurgical energy via first and second channels extending along a length of the housing to the distal end thereof. The distal end includes a reflector having a dielectric load operably coupled thereto and configured to receive at least a portion of the first conductor therein. In a first mode of operation, electrosurgical energy is transmitted to the first channel and reflected from the reflector to electrosurgically treat tissue. The reflector is configured to receive at least a portion of the second channel therein. In a second mode of operation, electrosurgical energy is transmitted to the second channel to dissect tissue.

20 Claims, 4 Drawing Sheets

Related U.S. Application Data continuation of application No. 13/477,320, filed on May 22, 2012, now Pat. No. 8,906,008.

(51) Int. Cl.
*A61B 18/18* (2006.01)
*A61B 18/00* (2006.01)
*A61B 18/12* (2006.01)

(52) U.S. Cl.
CPC ........... *A61B 2018/00607* (2013.01); *A61B 2018/00958* (2013.01); *A61B 2018/1273* (2013.01); *A61B 2018/1823* (2013.01); *A61B 2018/1869* (2013.01); *A61B 2018/1884* (2013.01); *A61B 2090/065* (2016.02)

(56) References Cited

U.S. PATENT DOCUMENTS

| | | |
|---|---|---|
| D266,842 S | 11/1982 | Villers et al. |
| D278,306 S | 4/1985 | McIntosh |
| D295,893 S | 5/1988 | Sharkany et al. |
| D295,894 S | 5/1988 | Sharkany et al. |
| D354,218 S | 1/1995 | Van de Peer |
| 5,405,346 A | 4/1995 | Grundy et al. |
| 5,582,610 A | 12/1996 | Grossi et al. |
| D424,693 S | 5/2000 | Pruter |
| D424,694 S | 5/2000 | Tetzlaff et al. |
| D425,201 S | 5/2000 | Tetzlaff et al. |
| 6,245,062 B1 | 6/2001 | Berube et al. |
| D449,886 S | 10/2001 | Tetzlaff et al. |
| D457,958 S | 5/2002 | Dycus et al. |
| D457,959 S | 5/2002 | Tetzlaff et al. |
| 6,471,696 B1 | 10/2002 | Berube et al. |
| D487,039 S | 2/2004 | Webster et al. |
| D496,997 S | 10/2004 | Dycus et al. |
| D499,181 S | 11/2004 | Dycus et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| D564,662 S | 3/2008 | Moses et al. |
| 7,393,352 B2 | 7/2008 | Berube |
| 7,410,485 B1 | 8/2008 | Fink et al. |
| D576,932 S | 9/2008 | Strehler |
| D594,736 S | 6/2009 | Esjunin |
| D594,737 S | 6/2009 | Kelly et al. |
| 7,611,508 B2 | 11/2009 | Yang et al. |
| D606,203 S | 12/2009 | Husheer et al. |
| D613,412 S | 4/2010 | DeCarlo |
| 7,828,799 B2 | 11/2010 | Desinger et al. |
| D634,010 S | 3/2011 | DeCarlo |
| 8,059,059 B2 | 11/2011 | Bonn |
| D681,810 S | 5/2013 | DeCarlo |
| 8,906,008 B2 | 12/2014 | Brannan et al. |
| 9,198,721 B2 | 12/2015 | Brannan et al. |
| 2001/0029368 A1 | 10/2001 | Berube |
| 2002/0193786 A1 | 12/2002 | Berube et al. |
| 2009/0230167 A1 | 9/2009 | Xiao et al. |
| 2010/0030207 A1* | 2/2010 | Hancock ............ A61B 18/1815 606/33 |
| 2010/0286687 A1 | 11/2010 | Feldberg et al. |

FOREIGN PATENT DOCUMENTS

| | | |
|---|---|---|
| CN | 101232852 A | 7/2008 |
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 3 648 515 A1 | 4/1995 |
| EP | 0 836 868 A2 | 4/1998 |
| EP | 0 882 955 A1 | 12/1998 |
| EP | 1159926 A3 | 3/2003 |
| EP | 1719451 A1 | 11/2006 |
| EP | 2258300 A1 | 12/2010 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 | 3/1996 |
| JP | 08252263 A | 10/1996 |
| JP | 09000492 A | 1/1997 |
| JP | 09010223 | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| SU | 166452 | 1/1965 |
| SU | 401367 A1 | 10/1973 |
| SU | 727201 A2 | 4/1980 |
| WO | 9944520 A1 | 9/1999 |

(56) References Cited

FOREIGN PATENT DOCUMENTS

| | | |
|---|---|---|
| WO | 02053221 A1 | 7/2002 |
| WO | 2006127847 A2 | 11/2006 |
| WO | 2009/040523 A2 | 4/2009 |
| WO | 2010/035831 A1 | 4/2010 |

OTHER PUBLICATIONS

European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM.Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. 1, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1 ):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
Urologix, Inc.—Medical Professionals: Targis.TM. Technology (Date Unknown). "Overcoming the Challenge" located at: (http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.

(56) References Cited

OTHER PUBLICATIONS

ValleyLab Brochure, "Electosurgery: A Historical Overview", Innovations in Electrosurgery, 1999.
Vallfors et al., "Automatically Controlled Bipolar Electrocoagulation—'COA-COMP" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992: pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
Extended European Search Report corresponding to EP No. 13 16 8717.0, completed Sep. 6, 2013 and mailed Sep. 19, 2013; (11 pp).
Extended European Search Report corresponding to EP 12168851.9, dated Aug. 16, 2012 (7 pp).
U.S. Appl. No. 14/011,414, filed Aug. 27, 2013, inventor: Ohri.
U.S. Appl. No. 14/011,438, filed Aug. 27, 2013, inventor: Ohri.
U.S. Appl. No. 14/242,019, filed Apr. 1, 2014, inventor: Brannan.
U.S. Appl. No. 14/242,048, filed Apr. 1, 2014, inventor: Prakash.
U.S. Appl. No. 14/281,264, filed May 19, 2014, inventor: Prakash.
U.S. Appl. No. 14/281,344, filed May 19, 2014, inventor: Shiu.
U.S. Appl. No. 14/300,824, filed Jun. 10, 2014, inventor: Behnke.
U.S. Appl. No. 14/300,871, filed Jun. 10, 2014, inventor: Bonn.
U.S. Appl. No. 14/306,865, filed Jun. 17, 2014, inventor: Brannan.
Geddes et al., "The Measurement of Physiologic Events by Electrical Impedence" Am. J. Mi, Jan. Mar. 1964, pp. 16-27.
U.S. Appl. No. 08/136,098, filed Oct. 14, 1993, Roger A. Stern.
U.S. Appl. No. 081483,742, filed Jun. 7, 1995, Roger A. Stern.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011 Behnke II, et al.
U.S. Appl. No. 13/237,488, filed Sep. 20, 2011, Behnke II, et al.
U.S. Appl. No. 13/267,369, filed Oct. 6, 2011, Prakash et al.
U.S. Appl. No. 13/268,143, filed Oct. 7, 2011, Kenlyn S. Bonn.
U.S. Appl. No. 13/281,605, filed Oct. 26, 2011, Prakash et al.
U.S. Appl. No. 13/290,462, filed Nov. 7, 2011, Kenlyn S. Bonn.
U.S. Appl. No. 13/298,461, filed Nov. 17, 2011, Buysse et al.
U.S. Appl. No. 13/344,753, filed Jan. 6, 2012, Lee et al.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,790, filed Jan. 6, 2012, Lee et al.
U.S. Appl. No. 13/351,463, filed Jan. 17, 2012, Smith et al.
U.S. Appl. No. 13/351,553, filed Jan. 17, 2012, Mahajan et al.
U.S. Appl. No. 13/358,129, filed Jan. 25, 2012, Joseph D. Brannan.
Alexander et al., "Magnetic Resonance Image-Directed Stereotactic Neurosurgery: Use of Image Fusion with computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic .RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division,(Products Price List), one page, Jul. 19, 2000.
Anonymous. Ground Cannulae, ISPG, New Milford, CT, (Advertisement) one page, Jul. 19, 2000.
B. Levy MD. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy MD. et al., "Update on Hysterectomy New Technologies and Techniques" OBG Management, Feb. 2003.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 070077819 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.

(56) References Cited

OTHER PUBLICATIONS

European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 070191719 dated Feb. 12, 2008.
European Search Report EP 07019174.7 dated Jan. 29, 2008.
European Search Report EP 07019178.8 dated Feb. 12, 2008.
European Search Report EP 070202813 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyms PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM. " Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw.cndot.Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Goldberg et al., "Image-guided Radiofrequency Tumor Ablation: Challenges and Opportunities—Part I", (2001) J Vasc. Interv. Radio!, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Humphries Jr. et al., "Finite-Element Codes to Model Electrical Heating and Non-L1near Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, " LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizes Use with Rigid-Compression. Mammographic Systems," Radiology 157(2):537-538.

(56) References Cited

OTHER PUBLICATIONS

Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDtech product literature (Dec. 1999) "FlexStrand": product description, 1 page.
MDtech product literature (Mar. 2000) I'D Wire: product description, 1 page.
European Search Report EP 09161502,1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 091693762 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 100017672 extended dated Jun. 18, 2010.
European Search Report EP 10004950.1 extended dated Jul. 2, 2010.
European Search Report EP 10004951.9 extended dated Jul. 2, 2010.
European Search Report EP 100055314 extended dated Sep. 24, 2010.
European Search Report EP 10005534.2 extended dated Sep. 17, 2010.
European Search Report EP 100063714 extended dated Nov. 11, 2010.
European Search Report EP 10008139.7 extended dated Nov. 30, 2010.
European Search Report EP 10008140.5 extended dated Dec. 28, 2010.
European Search Report EP 100085311 extended dated Dec. 20, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27,2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EpP 10185413.1 dated Mar. 14, 2011.
European Search Report EP 10191321.8 dated Apr. 7, 2011.
European Search Report EP 11000548.5 extended dated Apr. 14, 2011.
European Search Report EP 11004942 dated Sep. 23, 2011.
European Search Report EP 11174318.3 dated Nov. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 200t.
International Search Report PCT/US02/01890 dated Jul. 25, 2002.
International Search Report PCT/US02/11100 dated Jul. 16, 2002.
International Search Report PCT/US03/09483 dated Aug. 13, 2003.
Chinese Office Action and Search Report (with English translation), dated May 5, 2016, corresponding to Chinese Application No. 201310191354.4; 16 total pages.

\* cited by examiner

ELECTROSURGICAL INSTRUMENT

CROSS-REFERENCE TO RELATED APPLICATIONS

This application is a continuation application of U.S. patent application Ser. No. 14/564,896, filed on Dec. 9, 2014, now U.S. Pat. No. 9,198,721, which is a continuation application of U.S. patent application Ser. No. 13/477,320, filed on May 22, 2012, now U.S. Pat. No. 8,906,008, the entire contents of each of which are incorporated herein by reference.

BACKGROUND

Technical Field

The present disclosure relates to an electrosurgical instrument. More particularly, the present disclosure relates to a directional microwave energy instrument configured to electrosurgically treat tissue in two modes of operation; a first mode of operation to electrosurgically treat tissue; and a second mode of operation to dissect the tissue.

Description of Related Art

Standard surgical procedures for trauma, cancer and transplants in the kidney, liver, and like organs have several key shortcomings affecting efficacy, morbidity and mortality. In an effort to fully remove or resect an organ, the surgeon may be forced to breach the tissue causing a large amount of bleeding. Careful hemostasis can minimize blood loss and complications but is laborious and time consuming using the systems and methods known in the art. Uncontrollable bleeding, for example, is one of the leading causes that prevent such treatments from being offered to patients with cirrhotic livers.

Typical methods for creating resections and/or controlling bleeding and blood loss include scalpels, electrocautery, ultrasonic scalpels, argon beam coagulators, and radio frequency (RF) surface dissectors. Typically, a surgeon utilizes one of the aforementioned therapies, e.g., a scalpel, for creating resections and another one of the aforementioned therapies, e.g., an argon beam coagulator, to control bleeding. These therapies, however, in their present form have one or more potential drawbacks, such as, for example, a complete lack or partial inability to create a hemostatic or near-hemostatic resection plane with any significant depth (e.g., the devices utilized to control bleeding, typically, create a small footprint).

SUMMARY

As can be appreciated, a directional microwave and radio frequency energy instrument that is configured to electrosurgically treat tissue in two modes of operation to resect and dissect tissue may prove useful in the medical arts.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides an electrosurgical instrument. The electrosurgical instrument includes an elongated housing having proximal and distal ends. The proximal end configured to couple to a source of electrosurgical energy via first and second channels extending along a length of the housing to the distal end thereof. The distal end including a reflector having a dielectric load operably coupled thereto and configured to receive at least a portion of the first channel therein. In a first mode of operation electrosurgical energy is transmitted to the first channel and reflected from the reflector to electrosurgically treat tissue. The reflector is configured to receive at least a portion of the second channel therein. In a second mode of operation electrosurgical energy transmitted to the second channel to dissect tissue. The reflector may be formed from a conductive metal tube having a diagonal cross-cut at least partially through a width thereof.

The dielectric load may be shaped to complement a shape of the reflector. The dielectric load may be made from a material including, but not limited to ceramic, fluid and plastic. The dielectric load may include at least one aperture therein that is configured to receive at least a portion of the coaxial feed therein.

In certain instances, the first channel is in the form of a coaxial feed that includes an outer conductor, a dielectric extending past the outer conductor and an inner conductor extending past both the outer conductor and dielectric. In this instance, the inner conductor does not extend past the reflector.

In certain instances, the second channel may be in the form of an electrical lead including a monopolar electrode. In this instance, the monopolar electrode may be disposed at a distal tip of the reflector.

In certain instances, the electrosurgical instrument may also include a microwave block that is operably coupled to the distal end of the electrosurgical instrument adjacent the dielectric load. In this particular instance, the microwave block includes a dielectric distal portion and a conductive proximal portion. The microwave block may be configured to prevent electrosurgical energy from exiting a distal side of the reflector when the electrosurgical instrument is in the first mode of operation. The dielectric portion of the microwave block may include a dielectric constant that is less than a dielectric constant of the dielectric load of the distal end.

In certain instances, the electrosurgical instrument may also include a switch assembly that is supported on the housing and configured to place the electrosurgical instrument into the first and second modes of operation.

In certain instances, the electrosurgical instrument may also include a cooling assembly that operably couples to the electrosurgical instrument and circulates at least one coolant through the electrosurgical instrument to prevent the reflector and electrode from exceeding a predetermined temperature.

In certain instances, the electrosurgical instrument may also a sensor assembly that is configured to detect when the electrosurgical instrument contacts tissue. In this instance, the sensor assembly may be an optical sensor assembly, electrode impedance sensor assembly and acoustic transducer response assembly.

An aspect of the present disclosure provides an electrosurgical instrument. The electrosurgical instrument includes an elongated housing having proximal and distal ends. The proximal end is configured to couple to a source of electrosurgical energy via first and second channels extending along a length of the housing to the distal end thereof. A switch assembly is supported on the housing and is configured to place the electrosurgical instrument into first and second modes of operation. A reflector operably disposed at the distal end of the housing has a tapered configuration and is configured to provide an energy pattern in tissue proportional to a depth of the taper of the reflector. A dielectric load is shaped to complement a shape of the reflector for coupling the dielectric load to the reflector. The dielectric load is configured to receive at least a portion of the first channel therein. In the first mode of operation electrosurgical energy transmitted to the first channel is reflected from the reflector to electrosurgically treat tissue. The reflector is configured to receive at least a portion of the second channel therein. In the second mode of operation electrosurgical energy transmitted to the second channel to dissect tissue.

The dielectric load may be made from a material including, but not limited to ceramic, fluid and plastic. The dielectric load may include at least one aperture therein that is configured to receive at least a portion of the coaxial feed therein.

In certain instances, the first channel may be in the form of a coaxial feed that includes an outer conductor, a dielectric extending past the outer conductor and an inner conductor extending past both the outer conductor and dielectric. In this instance, the inner conductor does not extend past the reflector.

In certain instances, the second channel may be in the form of an electrical lead including a monopolar electrode. In this instance, the monopolar electrode may be disposed at a distal tip of the reflector.

In certain instances, the electrosurgical instrument may also include a microwave block that is operably coupled to the distal end of the electrosurgical instrument adjacent the dielectric load. In this particular instance, the microwave block includes a dielectric distal portion and a conductive proximal portion. The microwave block may be configured to shape electrosurgical energy exiting a distal side of the reflector and improve efficiency of the electrosurgical instrument when the electrosurgical instrument is in the first mode of operation. The dielectric portion of the microwave block may include a dielectric constant that is less than a dielectric constant of the dielectric load of the distal end.

BRIEF DESCRIPTION OF THE DRAWING

Various embodiments of the present disclosure are described hereinbelow with references to the drawings, wherein:

FIG. 5b is a schematic, cross-sectional view of the microwave balun depicted in FIG. 5a;

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful in the medical field to provide a directional microwave and radio frequency energy instrument that is configured to electrosurgically treat tissue in two modes of operation to resect and dissect tissue. In accordance with the instant disclosure, an electrosurgical instrument that couples to an electrosurgical energy source is configured to function in two or more modes of operation, a first mode that provides microwave energy to coagulate tissue (e.g., control bleeding) and a second mode that provides radio frequency energy to dissect the coagulated tissue (e.g., create a resection). The electrosurgical device in accordance with the instant disclosure allows a surgeon to perform both of these procedures with a single instrument.

Figure 1:
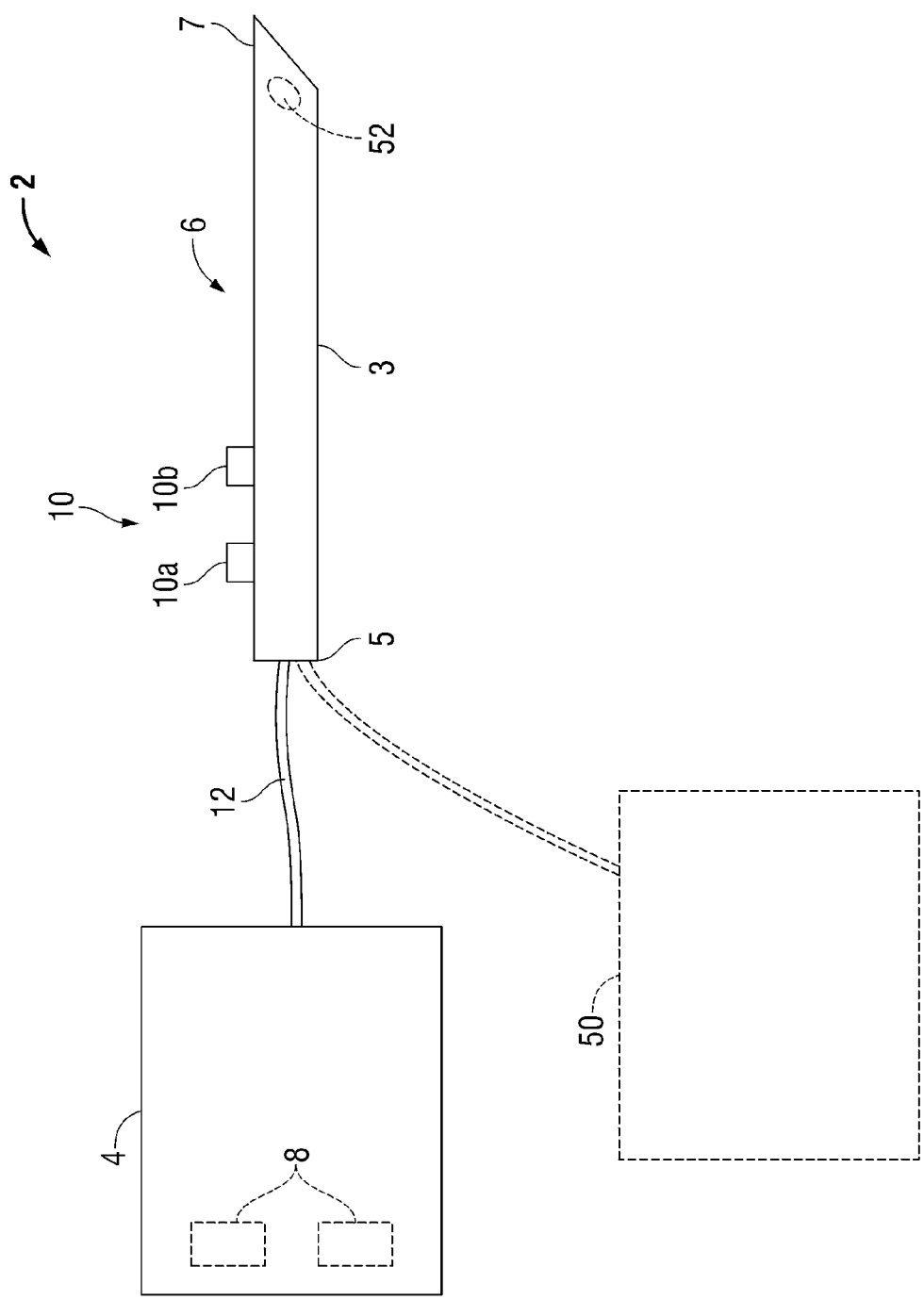
FIG. 1 is a schematic view of an electrosurgical system configured for use with an electrosurgical instrument according to an embodiment of the present disclosure.

Turning now to FIG. 1, an electrosurgical system 2 is illustrated including an electrosurgical energy source, e.g., a generator 4, and an electrosurgical instrument 6 in accordance with the instant disclosure.

Generator 4 is configured to generate electrosurgical energy in the form microwave energy and radio frequency energy. In embodiments, the generator 4 may be configured to also generate ultrasonic energy, thermal energy, etc. In accordance with the instant disclosure, frequencies of operation of the generator 4 range from about 915 MHz to about 8000 MHz. Other frequencies of operation of the generator 4 may be below 915 MHz and above 8000 MHz. One or more switches or buttons 8 (shown in phantom in FIG. 1) may be provided on the generator 4 to allow a surgeon to switch between first and second modes of operation. Alternately, and as in the illustrated embodiment, the electrosurgical instrument 6 may include one or more switches 10 (FIG. 1) thereon to allow a surgeon to switch between first and second modes of operation. Or, in certain instances, a footswitch (not explicitly shown) in operative communication with the generator 4 and/or the electrosurgical instrument 6 may be utilized to provide the aforementioned switching capabilities.

Electrosurgical instrument 6 includes a housing 3 having proximal and distal ends 5 and 7, respectively (FIG. 1). Housing 3 may be made from any suitable material including metal, plastic composite, ceramic, etc. In the illustrated embodiment, housing 3 is made from plastic composite. Housing 3 supports switching assembly 10 (and operative components associated therewith) thereon to provide the electrosurgical instrument 6 with hand-held capabilities, e.g., hand-held switching capabilities (FIG. 1).

Switching assembly 10 includes push-buttons 10a and 10b that respectively place the electrosurgical instrument 6 into the first and second modes of operation upon activation thereof.

Continuing with reference to FIG. 1, a cable 12 or the like couples the generator 4 to a housing 3 of the electrosurgical instrument 6 to provide electrosurgical instrument 6 with the capability of operating in the first and second modes of operation. To this end, cable 12 couples to proximal end 5 of housing 3 and includes a first channel in the form of a coaxial feed 14 and a second channel in the form of an electrical lead 16 (FIG. 2).

Figure 2:
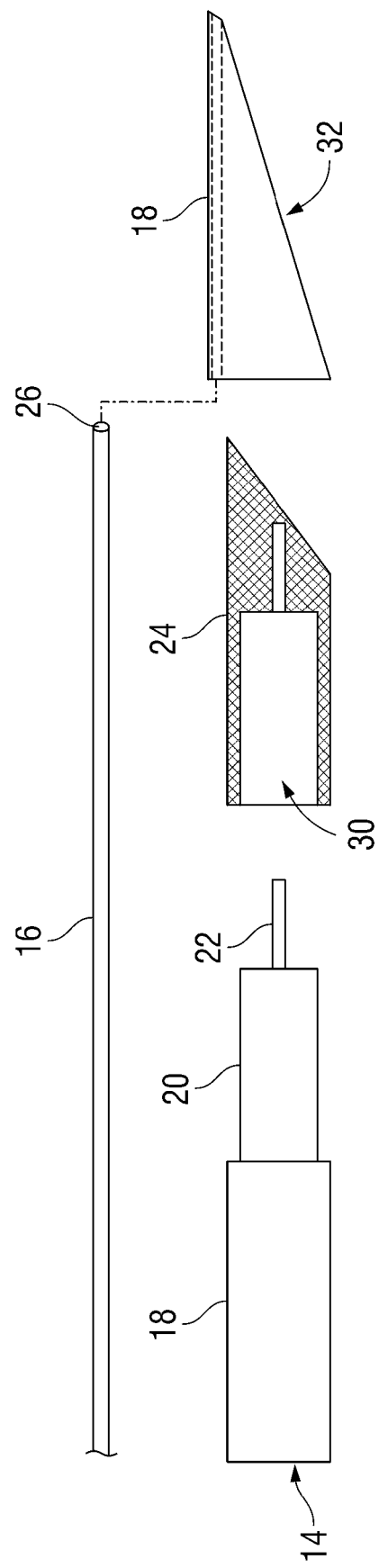
FIG. 2 is a schematic, exploded view of a distal end of the electrosurgical instrument depicted in FIG. 1 showing components separated.

Coaxial feed 14 is received at the proximal end 5 (FIG. 1) of the housing 3 for providing microwave energy thereto and includes an outer sheath (not explicitly shown), an outer conductor 18, a dielectric 20 that extends past the outer conductor and an inner conductor 22 that extends past both the outer conductor 18 and dielectric 20, as best seen in FIG. 2. This configuration of the coaxial feed 16 facilitates coupling the coaxial feed 14 to a dielectric load 24 (FIG. 2), as will be described in greater detail below.

Electrical lead 16 is received at the proximal end 5 (FIG. 1) of the housing 3 for providing radio frequency energy thereto and includes one or more electrodes, e.g., one or more monopolar electrodes 26, at a distal end thereof (FIG. 2).

Both of the coaxial feed 14 and electrical lead 16 extend along a length of the electrosurgical instrument 6 for coupling to the dielectric load 24 and a reflector 28, respectively (FIG. 2).

Referring to FIG. 2, dielectric load 24 is illustrated. Dielectric load 24 may be made from any suitable dielectric material including, but not limited to ceramic, plastic composite, fluid, etc. In the illustrated embodiment, dielectric load 24 is made from ceramic. Dielectric load 24 is shaped to complement the reflector 28 to facilitate coupling the dielectric load 24 to the reflector 28 during the manufacturing process of the electrosurgical instrument 6. The dielectric load 24 is coupled to the reflector 28 via one or ore suitable coupling methods. In the illustrated embodiment, a friction-fit or press-fit is utilized to couple the dielectric load 24 to the reflector 28. In particular, the reflector 28 includes a generally tubular configuration with a diameter that allows the dielectric load 24 to slide into the reflector 28 such that the dielectric load 24 is secured to the reflector 28.

Figure 3:
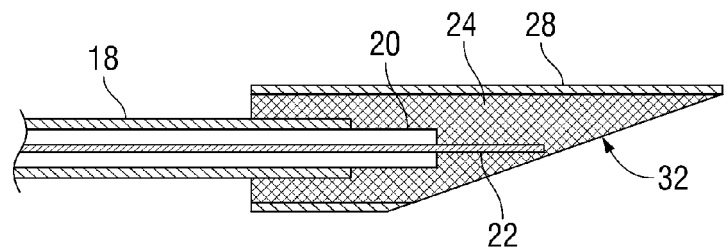
FIG. 3 is a schematic, side view of a coaxial feed and dielectric material of FIG. 2 in an assembled configuration.
Figure 4:
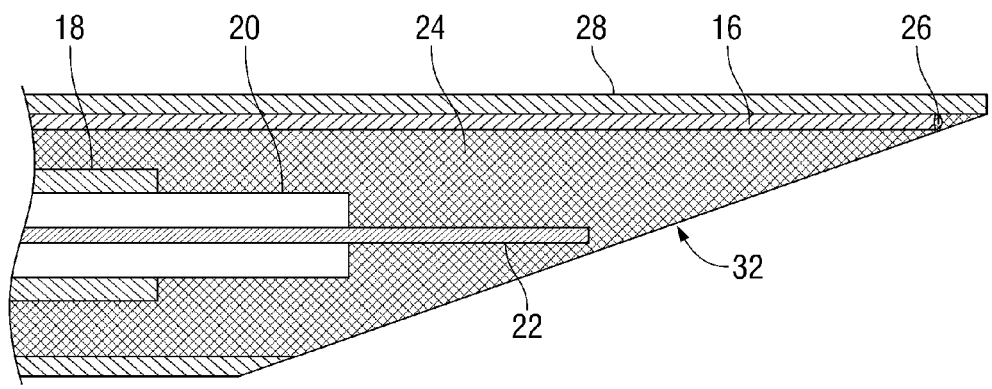
FIG. 4 is a schematic, side view of the coaxial feed, dielectric material and a reflector of FIG. 2 in an assembled configuration.
Figure 6:
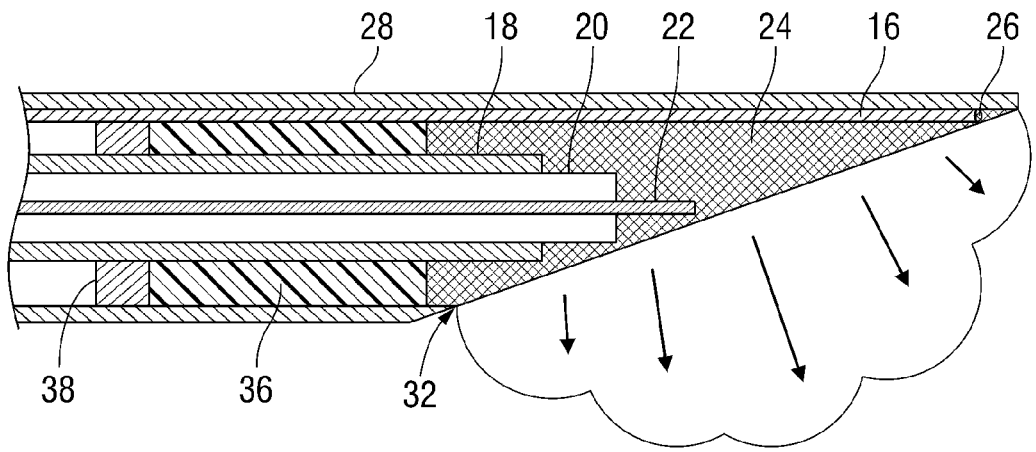
FIG. 6 is a schematic, side view of the distal end of the electrosurgical instrument depicted FIG. 1 with the microwave balun depicted in FIGS. 5a and 5b operably coupled thereto.
Figure 7:
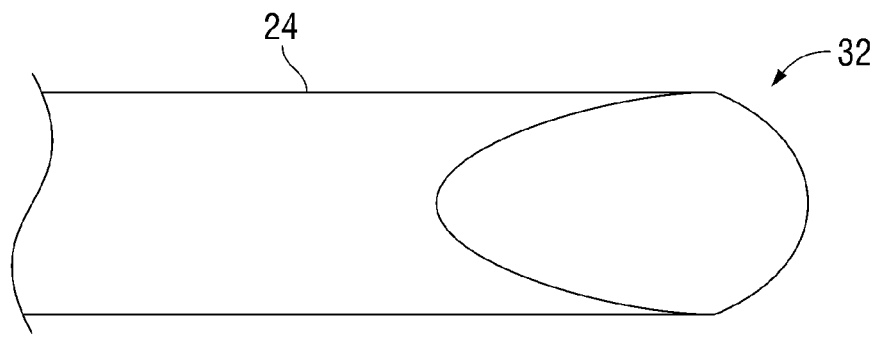
FIG. 7 is a schematic, bottom view of the reflector depicted in FIG. 2.

Dielectric load 24 includes a substantially solid configuration with an aperture 30 that is sized to receive the dielectric 20 and the inner conductor 22 therein, see FIGS. 2 and 3. In an assembled configuration, the dielectric 20 and inner conductor 22 are slid into the reflector and positioned adjacent a tapered, diagonal cut that extends along a distal face 32 of the reflector 28 (FIGS. 2-4 and 6). Positioning the inner conductor 22 at this location within the reflector 28 provides an energy pattern that is as long as the tapered distal face of the reflector 28, as best seen in FIG. 6.

Reflector 28 may be made from any suitable conductive material and, as noted above, includes a generally tubular configuration. In the illustrated embodiment, reflector 28 is made from metal that exhibits reflective properties to reflect the microwave energy in accordance with the instant disclosure. A tapered, diagonal cross-cut is provided through a width of the reflector 28 at the distal face 32 thereof. An angle of the cross-cut may be altered to achieve specific energy patterns that are reflected from the reflector 28 to electrosurgically treat tissue. In some embodiments, the reflector 28 may be configured to provide an energy pattern in tissue that is proportional to a depth of the taper of the reflector 28. Further, in certain instances, the distal face 32 may be selectively coated with conductive patterning to facilitate dissecting tissue during the second mode of operation.

Reflector 28 is configured to receive the electrical lead 16 including monopolar electrode(s) 26 therein, e.g., through an aperture (not explicitly shown) that extends through the reflector 28, such that the monopolar electrode(s) 26 is positionable adjacent a distal tip of the reflector 28 to emit radio-frequency energy to dissect tissue in the second mode of operation. Electrode(s) 26 may be secured within the aperture and to the reflector 28 via a press-fit, friction-fit, adhesive or other suitable coupling method.

Reflector 28 may be configured for coupling to the housing 3 by any suitable methods. In the illustrated embodiment, the reflector 28 is overmolded to the housing 3. Alternately, the reflector 28 may be press-fit or friction-fit to the housing 3, or an adhesive may be utilized to couple the reflector 28 to the housing 3.

Figure 5A:
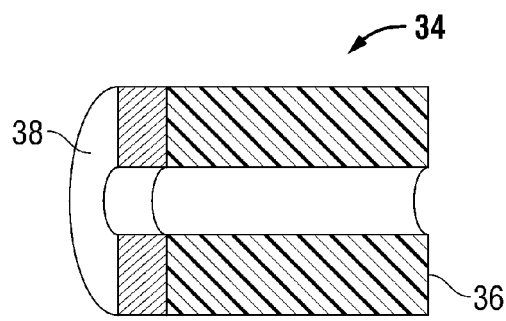
FIG. 5a is a schematic, proximal view of an optional microwave balun that may be utilized with the electrosurgical instrument depicted FIG. 1.
Figure 5B:
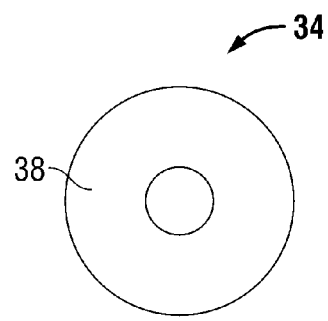

In embodiments, an optional microwave balun, e.g., a microwave block, choke short, impedance matching network of the like, (FIGS. 5A and 5B) may be operably coupled to a proximal end of the reflector 28 adjacent the dielectric load 24 (FIG. 6). In the illustrated embodiment, the microwave balun is in the form of a microwave block 34 that is configured to keep electrosurgical energy from exiting a distal side of the reflector 28 and control a shape of the radiating field emitted from reflector 28. Microwave block 34 may be configured to a fraction number of wavelengths, e.g., $\lambda/4$ wavelength. Microwave block 34 includes a generally elongated, annular configuration having a distal dielectric portion 36 and a proximal conductive portion 38 (see FIGS. 5A-5B). Distal dielectric portion 36 includes a dielectric that is lower than the dielectric load 24 and includes a higher loss factor than the dielectric load 24. In an assembled configuration the coaxial feed 14 is feed through the microwave block 34 such that the outer conductor 18 is in electrical communication with the proximal conductive portion 38, as best seen in FIG. 6. Configuring the distal dielectric portion 36 in this manner facilitates reducing the overall quality factor "Q" of the electrosurgical instrument 6.

Operation of the electrosurgical instrument 6 is described in terms of a liver resection. In use, electrosurgical instrument 6 is positioned adjacent tissue of interest, e.g., liver tissue. A surgeon may coagulate the tissue via pressing the push-button 10a to place the generator 4 in the first mode of operation. The microwave energy transmitted to the inner conductor 22 is reflected from the reflector 28 to electrosurgically treat the tissue. The reflective microwave energy provides a precise "footprint" on tissue, e.g., deeply penetrates tissue. The depth that the microwave energy penetrates tissue is determined by, inter alia, the angle of the distal face 32, frequency of operation and/or the power level that the generator 4 is set to.

A surgeon may, subsequently, dissect the electrosurgically treated tissue via pressing the push-button 10b to place the generator 4 in the second mode of operation. The microwave energy transmitted to the electrode(s) 26 is emitted therefrom to electrosurgically treat the tissue.

The electrosurgical instrument 6 overcomes the aforementioned shortcomings that are typically associated with conventional therapies for resection and dissecting tissue. That is, a surgeon can quickly and effectively resect and dissect tissue with a single instrument. As can be appreciated, this decreases blood loss and the time a patient needs to be under anesthesia during a resection and/or dissection procedure.

From the foregoing and with reference to the various figure drawings, those skilled in the art will appreciate that certain modifications can also be made to the present disclosure without departing from the scope of the same. For example, in certain embodiments, a cooling assembly 50 (shown in phantom in FIG. 1) may be operably coupled to the electrosurgical instrument 6 and configured to circulate at least one coolant through the electrosurgical instrument 6 to prevent the reflector 28 and/or electrode(s) 26 from exceeding a predetermined temperature.

In certain instances, the electrosurgical instrument 6 may also include surface contact detection capabilities configured to ensure that the electrosurgical instrument 6 is in adequate contact with tissue prior to enabling microwave and/or radio frequency energy to treat tissue. Surface contact capabilities may be provided by any suitable methods, such as, for example, a sensor assembly 52 (FIG. 1 shows a sensor assembly 52 in phantom for illustrative purposes) that is configured to detect when the electrosurgical instrument 6 contacts tissue. In this instance, the sensor assembly 52 may include one or more sensors (or combination of sensors) including, but not limited to, an optical sensor assembly, electrode impedance sensor assembly and acoustic transducer response assembly, etc.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument, comprising:
   a coaxial feed configured to couple to a source of electrosurgical energy;
   a balun disposed about a distal end of the coaxial feed; and
   an electrically conductive reflector operably coupled to the distal end of the coaxial feed, the reflector configured to radiate electrosurgical energy provided by the coaxial feed to treat tissue.

2. The electrosurgical instrument according to claim 1, further comprising a dielectric load coupled to the distal end of the coaxial feed.

3. The electrosurgical instrument according to claim 2, wherein the dielectric load is shaped to complement a shape of the reflector.

4. The electrosurgical instrument according to claim 2, wherein the dielectric load is made from a material selected from the group consisting of ceramic, fluid, and plastic.

5. The electrosurgical instrument according to claim 2, wherein the reflector defines a channel configured to receive the dielectric load therein and the dielectric load defines an aperture configured to receive the distal end of the coaxial feed therein.

6. The electrosurgical instrument according to claim 1, wherein the reflector is formed from a conductive metal tube having a diagonal cross-cut at least partially through a width thereof.

7. The electrosurgical instrument according to claim 1, wherein the coaxial feed includes:
   an outer conductor;
   a dielectric extending distally beyond the outer conductor; and
   an inner conductor extending distally beyond both the outer conductor and the dielectric of the coaxial feed.

8. The electrosurgical instrument according to claim 1, further comprising a monopolar electrode disposed at a distal end of the reflector and configured to electrically couple to a source of electrosurgical energy, wherein the monopolar electrode is configured to transmit radiofrequency energy to electrosurgically dissect tissue, and the coaxial feed is configured to transmit microwave energy to electrosurgically treat tissue.

9. The electrosurgical instrument according to claim 1, wherein the balun is configured to prevent electrosurgical energy from exiting the reflector.

10. The electrosurgical instrument according to claim 9, wherein the balun includes a dielectric portion and a conductive portion coupled to an outer conductor of the coaxial feedline.

11. An electrosurgical instrument, comprising:
    a coaxial feed configured to couple to a source of electrosurgical energy;
    a balun disposed about a distal end of the coaxial feed;
    a dielectric load defining an aperture configured to receive the distal end of the coaxial feed therein; and
    an electrically conductive reflector defining a channel configured to receive the dielectric load therein, the reflector configured to radiate electrosurgical energy provided by the coaxial feed to electrosurgically treat tissue.

12. The electrosurgical instrument according to claim 11, wherein the reflector is formed from a conductive metal tube having a diagonal cross-cut at least partially through a width thereof.

13. The electrosurgical instrument according to claim 11, wherein the dielectric load is shaped to complement a shape of the reflector.

14. The electrosurgical instrument according to claim 13, wherein the dielectric load is made from a material selected from the group consisting of ceramic, fluid, and plastic.

15. The electrosurgical instrument according to claim 11, wherein the coaxial feed includes:
    an outer conductor;
    a dielectric extending distally beyond the outer conductor; and
    an inner conductor extending distally beyond both the outer conductor and the dielectric of the coaxial feed.

16. The electrosurgical instrument according to claim 11, further comprising a monopolar electrode disposed at a distal end of the reflector and configured to electrically couple to a source of electrosurgical energy.

17. The electrosurgical instrument according to claim 16, wherein the monopolar electrode is configured to transmit radiofrequency energy to electrosurgically dissect tissue, and the coaxial feed is configured to transmit microwave energy to electrosurgically treat tissue.

18. The electrosurgical instrument according to claim 11, wherein the balun is configured to prevent electrosurgical energy from exiting the reflector.

19. The electrosurgical instrument according to claim 18, wherein the balun includes a dielectric portion and a conductive portion coupled to an outer conductor of the coaxial feed.

20. The electrosurgical instrument according to claim 18, wherein the dielectric portion of the balun includes a dielectric constant that is less than a dielectric constant of the dielectric load.

* * * * *